United States Patent [19]
Nakano et al.

[11] Patent Number: 5,231,186
[45] Date of Patent: Jul. 27, 1993

[54] QUATERNARY AMMONIUM SALTS

[75] Inventors: Shinji Nakano, Takatsuki; Satoshi Urano, Tanabecho, both of Japan

[73] Assignee: Nippon Paint Co., Ltd., Osaka, Japan

[21] Appl. No.: 855,390

[22] Filed: Mar. 20, 1992

[30] Foreign Application Priority Data

Mar. 22, 1991 [JP] Japan .................................. 3-83348

[51] Int. Cl.$^5$ .......................................... C07D 498/02
[52] U.S. Cl. ................................... 548/107; 548/102; 548/110; 548/218; 526/192
[58] Field of Search ............... 548/218, 107, 102, 110

[56] References Cited

U.S. PATENT DOCUMENTS

| | | | |
|---|---|---|---|
| 2,363,465 | 11/1944 | Senkus | 548/215 |
| 3,824,309 | 7/1974 | Schnegecberger et al. | 514/374 |
| 4,066,433 | 1/1978 | Hunsucker | 548/218 |
| 4,558,114 | 12/1985 | Goel | 548/218 |
| 4,725,611 | 2/1988 | Mahn et al. | 514/372 |
| 5,070,161 | 12/1991 | Nakano et al. | 526/193 |

FOREIGN PATENT DOCUMENTS

| | | | |
|---|---|---|---|
| 2344607 | 3/1975 | Fed. Rep. of Germany | 548/218 |
| 1596178 | 7/1970 | France | 548/218 |

OTHER PUBLICATIONS

Lewis, Chem. Abstr. vol. 98, entry 107197v (1982).
Walther et al. Chem. Abstr. vol. 95, entry 24222m (1980).
Antevnis et al. Chem. Abstr. vol. 82, entry 57403f (1974).
Chemishe Werke Chem. Abstr. vol. 74, entry 88091s (1970).
Antenvis et al. Org. Mag. Reson., vol. 6, pp. 362-366 (1974).
Lewis Jour. Flour. Chem. vol. 21, pp. 359-364 (1982).

*Primary Examiner*—Donald G. Daus
*Attorney, Agent, or Firm*—Mille, White, Zelano & Branigan

[57] ABSTRACT

Quaternary ammonium salts having a 2, 3, 5, 6-tetrahydroxazolo [2, 3-b] oxazole nucleus, such as 4-aralkyl or alkyl-2, 3, 5, 6-tetrahydroxazolo [2, 3-b] oxazolium salts are disclosed. These quarternary ammonium salts are useful a cationic polymerization initiator or proton-donating catalyst of the heat latent type to be incorporated heat-curable coating and other resinous compositions.

3 Claims, No Drawings

QUATERNARY AMMONIUM SALTS

BACKGROUND OF THE INVENTION

This invention relates to a novel class of quaternary ammonium salts which are useful as a cationic polymerization initiator.

A variety of cationic polymerization initiators are known including Friedel-Crafts catalysts such as aluminum chloride, boron trifluoride-ether complex, photodegradable onium salts (S, Se, Te), dially iodonium salts and the like. These known initiators are generally not selective with respect to the reaction temperature. Therefore, epoxy resins containing these initiators begin to cure even at room temperature.

Japanese Laid Open Patent Application (Kokai) Nos. 37003/83 and 37004/83 disclose another type of cationic polymerization initiators. They are aliphatic or aromatic sulfonium salts capable of generating carbonium cations upon heating to an elevated temperature. Initiators of this type are known as "heat-latent cationic polymerization initiator". Cation-polymerizable resins such as epoxy resins containing the heat-latent initiator are, therefore, normally inactive but capable of curing at a temperature above the cleaving temperature of the initiator. This provides a heat-curable, one-component epoxy resin composition having a greater storage-stability and a longer pot life.

Japanese Laid Open Patent Application (Kokai) No. 96169/88 and U.S. Pat. No. 5,070,161, both assigned to the assignee of this application, disclose heat-latent cationic polymerization initiators having an N-benzylpyridinium structure.

Unfortunately, the prior art heat-latent initiators suffer from a problem that their decomposition products are malodorous or their cleaving temperature is relatively high. This problem makes them impractical to use in coating compositions where such malodor or high baking temperatures are not desirable.

Accordingly, a strong need exists for a heat-latent cationic polymerization initiator which may eliminate or ameliorate this problem.

DISCLOSURE OF THE INVENTION

This invention provides, as a heat-latent cationic polymerization initiator, a quarternary ammonium salt of the formula I:

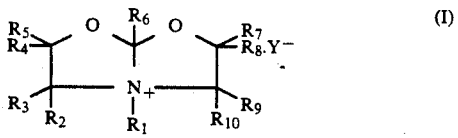

wherein
$R_1$ in a $C_1$-$C_{20}$ alkyl, alkenyl, alkynyl or aralkyl;
$R_2$, $R_3$, $R_9$ and $R_{10}$ are each a hydrogen atom, $C_1$-$C_{20}$ alkyl, alkenyl, alkynyl or aralkyl;
$R_4$, $R_5$, $R_7$ and $R_8$ are each a hydrogen atom, $C_1$-$C_{12}$ alkyl or aryl;
$R_6$ is an $C_1$-$C_{20}$ alky, alkenyl, alkynyl or aryl;
said alkyl, alkenyl, alkynyl, aralkyl and aryl may each have one or more substisuents selected from the group consisting of halo, alkoxy, nitro, amino, alkylamino, dialkylamino, cyano, alkoxycarbonyl and carbamoyl; and
$Y^-$ is a halide, perchlorate, permanganate, carboxylate, organic sulfonate or organic phosphate anion, or an anion of the formula: $MX_n^-$ wherein M is an element selected from the group consisting of As, Sb, B and P, X is a halogen atom, and n equals to the valence of element M minus 1.

Particularly emphasized are those compounds of the formula I wherein $R_2$-$R_5$ and $R_7$-$R_{10}$ are each a hydrogen atom, $R_6$ is methyl, $R_1$ is an alkl or aralkyl, and $Y^-$ is $MX_n^-$.

The compounds of the present invention may be synthesized by reacting a compound of the formula: $R_1$-$Y'$ wherein $R_1$ is as defined and $Y'$ is a halogen atom with a bicyclic amide acetal of the formula II:

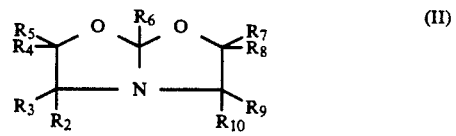

wherein all symbols are as defined, and then exchanging the halide anion of the resulting quaternary ammonium halide with an appropriate anion where the quarternary ammonium salt with $Y^-$ anion other than the halide anion is desired.

The bicyclic amide acetal of the formula II has a 2, 3, 5, 6-tetrahydroxazolo-[2,3-b] oxazole nucleus of the formula:

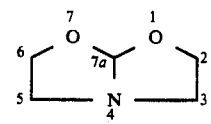

and may be synthesized by reacting a nitrile with a dialkanolamine as reported in e.g. German Patent No. 2,344,607.

The quaternary ammonium salts of the present invention are thermally cleaved at an elevated temperature to produce a carbonium cation or proton when an excess of water is present. However, they are substantially inactive at ambient temperatures. Therefore, they may be used as a curing or polymerization catalyst in one-component epoxy- or proton-catalyzed resin compositions where a prolonged storage stability as well as odorless decomposition products are desired.

The following examples are intended to further illustrate the present invention without limiting thereto.

EXAMPLE 1

4-(4-Methoxybenzyl)-7a-methyl-2, 3, 5, 6-tetrahydroxazolo [2, 3-b] oxazolium hexafluoroantimonate 12.9 g (0.1 mole) of 7a-methyl-2, 3, 5, 6-tetrahydroxazolo [2, 3-b] oxazole and 15.7 g (0.1 mole) of 4-methoxybenzyl chloride were reacted in 40 ml of methanol at 40° C. for 20 hours. After the reaction, the solvent was evaporated in vacuo and the residue was extracted with ether/water to remove unreacted reactants in the etherial layer. To the aqueous layer containing the resulting oxazolium chloride was added 25.87 g (0.1 mole) of sodium hexafluoroantimonate. The resulting crystals were suction filtered, washed and dried to give the title compound.

NMR:2.0 ppm (s, 3H, Me), 3.6 ppm (s, 3H, MeO), 3.9–4.8 ppm (m, 8H,CH$_2$), 7.0–7.1 ppm (d, 2H, Ph), 7.6–7.7 ppm (d, 2H, Ph).

EXAMPLE 2

4-(4-Methylbenzyl)-7a-methyl-2, 3, 5, 6-tetrahydroxazolo [2, 3-d] oxazolium hexafluorophosphate Analogous to Example 1, the title compound was prepared starting from 7a-methyl-2, 3, 5, 6-tetrahydroxazolo [2, 3-b] oxazole, 4-methylbenzyl chloride and sodium hexafluorophosphate.

NMR: 2.0 ppm (s, 3H, Me), 2.3 ppm (s, 3H, Me), 3.9–4.8 ppm (m, 8H, CH$_2$), 7.2–7.3 ppm (d, 2H, Ph), 7.5 ppm (d, 2H, Ph)

EXAMPLE 3

4, 7a-dimethyl-2, 3, 5, 6-tetrahydroxazole [2, 3-b] oxazolium tetrafluoroborate

Analogous to Example 1, the title compound was prepared starting from 7a-methyl-2, 3, 5, 6-tetrahydroxazolo [2, 3-b] oxazole, methyl iodide and sodium tetrafluoroborate.

NMR: 1.7 ppm (s, 3H, Me), 3.2 ppm (s, 3H, Me), 3.7–4.5 ppm (m, 8H, CH$_2$)

EXAMPLE 4

4-(4-methoxybenzyl)-7a-methyl-2, 3, 5, 6-tetrahydroxazolo [2, 3-b] oxazolium p-toluenesulfonate The title compound was prepared by replacing sodium p-toluenesulfonate for sodium hexafluoroantimonate in Example 1.

NMR: 2.0 ppm (s, 3H, Me), 2.3 ppm (s, 3H, Me), 3.6 ppm (s, 3H, MeO), 3.9–4.8 ppm (m, 8H, CH$_2$), 7.0–7.7 ppm (m, 8H, Ph)

EXAMPLE 5

4-(4-methylbenzyl)-7a-methyl-2, 3, 5, 6-tetrahydroxazolo [2, 3-b] oxazolium trifluoromethanesulfonate The title compound was prepared by replacing sodium trifluoromethanesulfonate for sodium hexafluorophosphate in Example 2.

NMR: 2.0 ppm (s, 3H, Me), 2.3 ppm (s, 3H, Me), 3.9–4.8 ppm (m, 8H, CH$_2$), 7.2–7.3 ppm (d, 2H, Ph), 7.5 ppm (d, 2H, Ph)

EXAMPLE 6

4-(4-methoxybenzyl)-7a-methyl-2, 3, 5, 6-tetrahydoxazolo [2, 3-b] oxazolium acetate The title compound was prepared by replacing sodium acetate for sodium hexafluoroantimonate in Example 1.

NMR: 1.3 ppm (s, 3H, Me), 2.0 ppm (s, 3H, Me), 2.3 ppm (s, 3H, Me), 3.6 ppm (s, 3H, MeO), 3.9–4.8 ppm (m, 8H, CH$_2$), 7.0–7.7 ppm (m, 8H, Ph)

We claim:

1. A quaternary ammonium salt of the formula I:

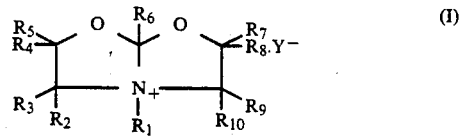

wherein $R_1$ is 4-methylbenzyl or 4-methoxybenzyl;

$R_2$, $R_3$, $R_4$, $R_5$, $R_7$, $R_8$, $R_9$ and $R_{10}$ are each a hydrogen atom;

$R_6$ is methyl; and $Y^-$ is an anion of the formula: $MX_n^-$ wherein M is an element selected from the group consisting of As, Sb, B and P, X is fluorine, and n is equal to the valence of element M minus 1.

2. The quaternary ammonium salt of claim 1, which is 4-(4-methoxybenzyl)-7a-methyl-2, 3, 5, 6-tetrahydroxazolo [2, 3-b] oxazolium hexafluoroantimonate.

3. The quaternary ammonium salt of claim 1, which is 4-(4-methylbenzyl)-7a-methyl-2, 3, 5, 6-tetrahydroxazolo [2, 3-b] oxazolium hexafluorophosphate.

* * * * *